United States Patent [19]

Spencer

[11] Patent Number: 4,582,645

[45] Date of Patent: Apr. 15, 1986

[54] CARBONATE PRODUCTION

[75] Inventor: Michael S. Spencer, Stockton-on-Tees, England

[73] Assignee: Imperial Chemical Industries PLC, London, England

[21] Appl. No.: 648,678

[22] Filed: Sep. 10, 1984

[30] Foreign Application Priority Data

Oct. 4, 1983 [GB] United Kingdom ............... 8326556

[51] Int. Cl.$^4$ ...................... C07C 68/06; C07C 68/08
[52] U.S. Cl. ..................................... 558/277; 210/691
[58] Field of Search ............... 260/463; 210/690, 691, 210/692

[56] References Cited

U.S. PATENT DOCUMENTS

| | | | |
|---|---|---|---|
| 2,834,799 | 4/1958 | Sowa | 260/463 |
| 3,952,045 | 4/1976 | Gaenzler et al. | 260/463 |
| 4,213,913 | 7/1980 | de Rosset | 260/248.5 |
| 4,218,391 | 8/1980 | Romano et al. | 260/463 |
| 4,257,885 | 3/1981 | Grose et al. | 210/691 |
| 4,309,281 | 1/1982 | Dessau | 210/690 |
| 4,327,035 | 4/1982 | Heitz et al. | 260/463 |

FOREIGN PATENT DOCUMENTS 0085347 1/1983 European Pat. Off. .
1593704 7/1981 United Kingdom .

OTHER PUBLICATIONS

Flanigen et al.: "Silicalite, A New Hydrophobic Crystalline Silica Molecular Sieve", Nature, vol. 271, Feb. 9, 1978, pp. 512–516.

Yamazaki et al.: "Polycarbonate, -Urethane and -Urea from Carbon Dioxide and Carbonates", Polymer Preprints, 20 (1979), pp. 146–149.

Primary Examiner—Donald G. Daus
Assistant Examiner—Stephen M. Kapner
Attorney, Agent, or Firm—Cushman, Darby & Cushman

[57] ABSTRACT

A solution of a di-alkyl carbonate, e.g. dimethyl carbonate, in the corresponding alcohol, e.g. methanol, is concentrated by contacting the solution with a hydrophobic zeolite e.g. silicalite. The di-alkyl carbonate is absorbed preferentially. Where the solution also contains water, e.g. as in the case of the products from certain di-alkyl carbonate synthesis reactions, the water can be removed using a hydrophilic zeolite prior to recycle of the alcohol.

10 Claims, No Drawings

CARBONATE PRODUCTION

This invention relates to carbonate production and in particular to the production of di-alkyl carbonates.

Various methods have been proposed for the production of di-alkyl carbonates, including the reaction of an alcohol (i) with carbon monoxide and oxygen in the presence of a suitable catalyst, e.g. a copper halide—see for example U.S. Pat. Nos. 3,952,045 and 4,218,391, (ii) with carbon dioxide using an organo tin compound as catalyst—see "Polymer Preprints" 20 (1979) page 146, or (iii) with urea or a urethane—see for example U.S. Pat. Nos. 2,834,799 and 4,327,035.

Other routes are also known which also involve the use of the corresponding alcohol as the starting material. Since the conversions and yields in the above processes are generally low, the alcohol is often employed in a substantial excess and so the product di-alkyl carbonate is produced in the form of a dilute solution thereof in the alcohol. For example in the reaction of methanol and carbon dioxide, the conversion is such that, even at high pressures, the product solution contains about 0.5% by weight of dimethyl carbonate at a pressure of 50 bar, rising to 2-3% by weight at a pressure of 1000 bar.

Separation of the alcohol and di-alkyl carbonate by distillation from such dilute solutions is uneconomic because of the relatively large proportion of alcohol that has to be removed. In addition, in some of the synthesis processes, water is formed as a by-product and this further hampers such separation, in some cases, as a result of azeotrope formation.

We have devised a simple method for the concentration of such dilute solutions to a level where distillation separation methods become more economic.

Accordingly the present invention provides a method of concentration of a solution of a di-alkyl carbonate in an alcohol comprising contacting the solution with a hydrophobic zeolite into which the di-alkyl carbonate is preferentially sorbed to give a sorbed mixture richer in di-alkyl carbonate than said solution, and subsequently desorbing said mixture from the zeolite.

The zeolite may be silicalite (see "Nature" 271, Feb. 9, 1978, pages 512-516) or other hydrophobic zeolite: such hydrophobic zeolites are characterised by a low alumina to silica molar ratio, generally below about 0.05. The ratio may be as small as 0.003 or even lower: indeed in silicalite the ratio may be below 0.001. These hydrophobic zeolites have intermediate sized pores, typically in the range 5 to 10 Å. Examples of suitable zeolites include silicalite, and zeolites of the ZSM 5, NU-1, EU-1, and EU-2 types, and others of ZSM, NU and EU series.

While these hydrophobic zeolites sorb alcohols, we have found that di-alkyl carbonates are sorbed preferentially: thus typically the mixture sorbed from a solution containing 2% by weight of the di-alkyl carbonate may contain about 20% by weight of di-alkyl carbonate.

The sorption can conveniently be effected by passing the solution through a column packed with the zeolite at a suitable temperature, e.g. 10° to 50° C. The sorption step may be conducted at any convenient pressure, but where high pressures are employed in the di-alkyl carbonate synthesis, process engineering advantages may result if the sorption step is also performed under high pressure.

The zeolite sorbs an alcohol/di-alkyl carbonate mixture, leaving an effluent stream comprising the alcohol have only a very small di-alkyl carbonate content. This alcohol stream can then be recycled to the di-alkyl carbonate synthesis process.

In some of the dialkyl-carbonate synthesis processes, water is formed as a by-product as mentioned hereinbefore. While the presence of water has little effect on the sorption process, it may be preferred to remove the water e.g. by sorption on to a hydrophilic zeolite, e.g. a small pore (3–5 Å) zeolite having an alumina/silica molar ratio in the range 0.1 to 0.5, such as a zeolite of the A, 3A, 4A and 5A families. Such water removal may be effected prior to sorption of the di-alkyl carbonate or on the effluent alcohol stream prior to recycle thereof. Where water removal is effected subsequent to the sorption of the di-alkyl carbonate, in order to improve the efficiency of the di-alkyl carbonate sorption, it is preferred to subject the hydrophobic zeolite to a wash with an aqueous acid prior to sorption of the di-alkyl carbonate. The alcohol/di-alkyl carbonate solution may also contain soluble catalysts, e.g. tin or copper complexes.

The concentrated di-alkyl carbonate solution can be recovered from the hydrophobic zeolite by desorption simply by heating, e.g. at 50° to 200° C. or by flushing out using a solvent, e.g. a hydrocarbon, that is sorbed more preferentially than the di-alkyl carbonate/alcohol mixture. The flushing solvent can subsequently be desorbed by heating so that the hydrophobic zeolite can be re-used. Where the sorption step of the di-alkyl carbonate by the hydrophobic zeolite is performed at high pressures, desorption of the di-alkyl carbonate containing mixture may alternatively be effected by reducing the pressure.

While the process of the invention may be used for solutions of any di-alkyl carbonate in its corresponding alcohol, it is of particular utility in the production of di-alkyl carbonates in which the alkyl groups contain 1 to 5 carbon atoms. It is most preferably used for the concentration of solutions of dimethyl or diethyl carbonates in methanol or ethanol respectively.

The dilute di-alkyl carbonate solution preferably contains 0.1 to 10% by weight of the di-alkyl carbonate.

The invention is illustrated by the following examples.

EXAMPLE 1

A sample of silicalite was shown to be highly crystalline by X-ray diffraction and to have an alumina/silica mole ratio of about 0.0009 by chemical analysis. It was calcined in air at 550° C. for 24 hours for activation. 2.5 g of the silicalite was put in a vessel and 10 ml of a solution of dimethyl carbonate in methanol (21.4 g dimethyl carbonate/l) was added at ambient temperature. The change in dimethyl carbonate concentration in solution (due to sorption by the silicalite) was followed by gas chromatographic analysis of samples of solution and so the amount of dimethyl carbonate sorbed by silicalite could be calculated. The results are given in Table 1.

TABLE 1

| Time (minutes) | Dimethyl carbonate sorbed on silicalite (g) |
| --- | --- |
| 0 | 0 |
| 1 | 0.073 |
| 18 | 0.093 |

TABLE 1-continued

| Time (minutes) | Dimethyl carbonate sorbed on silicalite (g) |
|---|---|
| 33 | 0.077 |
| 48 | 0.107 |
| 63 | 0.098 |

These results show that selective sorption of dimethyl carbonate was rapid. Almost 50% of the dimethyl carbonate originally present in solution was taken up by the silicalite. Methanol sorption by silicalite in the absence of other sorbates is about 0.19 cm$^3$g$^{-1}$ ie about 0.15 g methanol/g silicalite. (See the aforesaid "Nature" reference at page 514). Thus the sorbed dimethyl carbonate occupied about 20% of the pore volume available to methanol, so the concentration of dimethyl carbonate was enhanced by at least 10 times.

EXAMPLE 2

A sample of silicalite from Example 1 was washed with an aqueous acid and then with water. Example 1 was repeated with this sample of silicalite. The results are given in Table 2.

TABLE 2

| Time (minutes) | Dimethyl carbonate sorbed on silicalite (g) |
|---|---|
| 0 | 0 |
| 1 | 0.079 |
| 10 | 0.126 |
| 18 | 0.119 |
| 29 | 0.115 |
| 46 | 0.089 |
| 56 | 0.116 |
| 68 | 0.130 |

Sorption was greater than in Example 1, with about 25% of the pore space available to methanol being occupied by dimethyl carbonate.

EXAMPLE 3

Example 1 was repeated but the solution of dimethyl carbonate in methanol also contained 0.5% v/v of water. The results are given in Table 3.

TABLE 3

| Time (minutes) | Dimethyl carbonate sorbed on silicalite (g) |
|---|---|
| 0 | 0 |
| 1 | 0.048 |
| 8 | 0.060 |
| 16 | 0.057 |
| 30 | 0.064 |
| 40 | 0.084 |
| 50 | 0.067 |
| 60 | 0.089 |

Rapid and selective sorption occurred as in Example 2 but the extent of sorption was decreased by the presence of water.

EXAMPLE 4

Example 2 was repeated but with the same methanol/dimethyl carbonate/water solution as in Example 3. The results are given in Table 4. Comparison with Table 2 shows that water had no significant effect on sorption in the acid-washed silicalite.

TABLE 4

| Time (minutes) | Dimethyl carbonate sorbed in silicalite (g) |
|---|---|
| 0 | 0 |
| 1 | 0.064 |
| 10 | 0.087 |
| 19 | 0.102 |
| 34 | 0.127 |

In all the above examples, the dimethyl carbonate/methanol mixture could be de-sorbed from the silicalite by heating or by flushing with a hydrocarbon such as hexane.

I claim:

1. A method of concentrating a solution of a di-alkyl carbonate in an alcohol comprising
   contacting said solution with a hydrophobic zeolite, said zeolite having an alumina to silica molar ratio below 0.05, into which the di-alkyl carbonate is preferentially sorpted to give a sorpted mixture richer in di-alkyl carbonate than said solution, and subsequently
   desorbing said mixture from the zeolite.

2. A method according to claim 1 wherein the zeolite has an alumina to silica molar ratio below 0.003.

3. A method according to claim 1 wherein the zeolite is silicalite.

4. A method according to claim 1 wherein said solution contacted with said zeolite contains water, said process further comprising washing said zeolite, prior to contact with said solution, with an aqueous acid.

5. A method according to claim 3 wherein said solution contacted with said zeolite contains water, said process further comprising washing said zeolite, prior to contact with said solution, with an aqueous acid.

6. A method according to claim 1 wherein said di-alkyl carbonate is dimethyl carbonate and said alcohol is methanol.

7. A method according to claim 3 wherein said di-alkyl carbonate is dimethyl carbonate and said said alcohol is methanol.

8. A process for producing di-alkyl carbonate from an alcohol using an excess of said alcohol, comprising the step of concentrating the solution of di-alkyl carbonate in said alcohol by a method according to claim 1.

9. A process according to claim 8 wherein the solution of di-alkyl carbonate in the alcohol produced in the di-alkyl carbonate synthesis step also contains water, said process further comprising recycling to said synthesis step the alcohol remaining after sorption of di-alkyl carbonate therefrom by said hydrophobic zeolite, and removing water by sorption by contact with a hydrophilic zeolite prior to said alcohol recycle.

10. A process according to claim 9 wherein said water is removed by contacting said solution produced in the di-alkyl carbonate synthesis step with said hydrophilic zeolite prior to sorption of said di-alkyl carbonate with said hydrophilic zeolite.

* * * * *